(12) United States Patent
Sasank et al.

(10) Patent No.: US 10,074,893 B2
(45) Date of Patent: Sep. 11, 2018

(54) DEVICE USED TO REDUCE ELECTROMAGNETIC RADIATIONS

(71) Applicant: SRIHITHA SHOPPING SERVICES PVT. LTD, Hyderabad (IN)

(72) Inventors: Ravi Sasank, Hyderabad (IN); Kishore Kumar Reddy G, Hyderabad (IN)

( * ) Notice: Subject to any disclaimer, the term of this patent is extended or adjusted under 35 U.S.C. 154(b) by 215 days.

(21) Appl. No.: 15/033,651

(22) PCT Filed: Feb. 9, 2015

(86) PCT No.: PCT/IB2015/050955
§ 371 (c)(1),
(2) Date: May 2, 2016

(87) PCT Pub. No.: WO2015/118501
PCT Pub. Date: Aug. 13, 2015

(65) Prior Publication Data
US 2016/0336647 A1    Nov. 17, 2016

(30) Foreign Application Priority Data

Feb. 10, 2014    (IN) .............................. 596/CHE/2014

(51) Int. Cl.
*H01Q 1/24*    (2006.01)
*A61N 1/16*    (2006.01)
*H05K 9/00*    (2006.01)
*H01Q 15/00*    (2006.01)
*H01Q 1/48*    (2006.01)
(Continued)

(52) U.S. Cl.
CPC ............... *H01Q 1/245* (2013.01); *A61N 1/16* (2013.01); *H01Q 1/243* (2013.01); *H01Q 1/48* (2013.01); *H01Q 1/50* (2013.01); *H01Q 15/0026* (2013.01); *H01Q 17/002* (2013.01); *H05K 9/0064* (2013.01); *H05K 9/0081* (2013.01); *H05K 9/0088* (2013.01)

(58) Field of Classification Search
CPC ............... H01Q 1/50; H01Q 1/24; H01Q 1/38
USPC ...................................................... 343/860
See application file for complete search history.

(56) References Cited

U.S. PATENT DOCUMENTS 7,847,753 B2 * 12/2010 Ishibashi ................ H01Q 1/243
                                                                                           343/702
2005/0174290 A1 * 8/2005 Huang ................... H01Q 1/243
                                                                                         343/700 MS
(Continued)

*Primary Examiner* — Huedung Mancuso

(57) ABSTRACT

Exemplary embodiments of the present subject matter is directed towards a device used to reduce electromagnetic radiations comprising a electromagnetic resistance sheet including a first layer and a third layer positioned at front and rear portions of the electromagnetic resistance metallic sheet configured to convert received excess radio frequency radiations of electronic signals to electromagnetic field signals and ground the converted electromagnetic field; and cloud signals for avoiding the transmission of radiations into the human body and environment. The first layer and the third layer coated with plurality of chemical elements. The electromagnetic resistance sheet also includes a second layer positioned between the first layer and the third layer coated with plurality of metallic elements to provide anti corrosion of the electromagnetic resistance sheet in the transmission of radiations.

10 Claims, 3 Drawing Sheets

(51) Int. Cl.
*H01Q 1/50* (2006.01)
*H01Q 17/00* (2006.01)

(56) References Cited

U.S. PATENT DOCUMENTS

| | | | | |
|---|---|---|---|---|
| 2007/0042654 | A1* | 2/2007 | Arakawa | H05K 9/0096 442/1 |
| 2009/0051258 | A1* | 2/2009 | Kim | H01J 11/10 313/112 |
| 2010/0019988 | A1* | 1/2010 | Kim | H01P 1/20381 343/911 R |

* cited by examiner

DEVICE USED TO REDUCE ELECTROMAGNETIC RADIATIONS

TECHNICAL FIELD

The present disclosure relates to a field of reducing impact of electromagnetic radiations on human health. More particularly, the present invention relates to a device used to minimize a negative impact of electromagnetic field radiations emitted by electronic equipments.

BACKGROUND

Mobile phones and all the electrical equipment now commonly in use have high frequency radio waves to split the genetic molecules, causing skin cancer and brain tumors, cataracts and other diseases can also cause the slightest insomnia, headaches. This growing use of wireless communication in the last decade has introduced concerns about health risks from the so called man-made electromagnetic smog from Microwave Radiations. Various epidemiological and experimental studies have been carried out and the results have shown to have a close relation between biological effects on living beings and electromagnetic radiation. The electromagnetic radiation is also generated by satellite television boxes, televisions, blue-tooth, Wi-Fi, refrigerators and the like. The development of mobile communication technology, the phone has become the most convenient and effective communication tool. However, people using the mobile phones were somewhat worried about cell phone radiation.

In the light of aforementioned discussion there exists a need for developing a device used to minimize the excess and unwanted radiation generated by the electronic equipments.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Exemplary aspect of the present subject matter is to provide an optimized anti radiation safety device to reduce the emitted electromagnetic radiation.

Another exemplary aspect of the present subject matter is to provide a chip which effectively reduces the exposure of humans to electromagnetic radiation that are continuously emitted and absorbed while using mobile phones or other electrical equipments.

Another exemplary aspect of the present subject matter is to use a material in the product that absorbs and reduces the effect when placed on the mobile or any such EMR emitting object.

Another exemplary aspect of the present subject matter is to provide a chip which acts as a signal filter and signal repeater only allowing the required signal.

Yet another exemplary aspect of the present subject matter is to provide a small chip which can be affixed to the electronic equipments.

Still another exemplary aspect of the present subject matter is to use the device as a signal booster and electromagnetic field grounding substance.

Exemplary embodiment of the present disclosure is directed towards a device used to reduce electromagnetic radiations. According to a first aspect, the device includes an electromagnetic resistance sheet comprising a first layer and a third layer positioned at front and rear portions of the electromagnetic resistance sheet configured to convert received excess radio frequency radiations of electronic signals to electromagnetic field signals and ground the converted electromagnetic field and/or cloud signals for avoiding the transmission of radiations into the human body. The first layer and the third layer coated with plurality of chemical elements.

According to the first aspect, the electromagnetic resistance sheet includes a second layer positioned between the first layer and the third layer coated with plurality of metal elements to provide anti corrosion of the laminated sheet in the transmission of radiations.

According to a second aspect a method to reduce electromagnetic radiations is disclosed. According to the second aspect, the method includes cleansing an electromagnetic resistance sheet with a chemical element dissoluble in water and dipped into a high viscous fluid comprising a chemical element. The metal strand integrated in the electromagnetic resistance sheet affixed with the chemical element of the high viscous liquid to avoid anti corrosions.

According to the second aspect, the method includes mixing a predetermined amount of inorganic compound in low viscous liquid to form a solution. The predetermined amount of chemical element coupled with cathode and anode dipped into the mixed solution to dissolve the chemical element in the viscous liquid and forms a light yellow solution.

According to the second aspect, the method includes inserting a predetermined length of the electromagnetic resistance sheet coupled with anode into the boiled solution. The electromagnetic resistance sheet receives power from the boiled solution along with the chemical element dissolved in the solution and leaves the color less solution.

According to the second aspect, the method includes cleansing the electromagnetic resistance sheet with low viscous liquid to completely cleanse out the inorganic compound on the electromagnetic resistance sheet received from the chemical element dissolved in the solution for protecting the biological health of the human.

According to the second aspect, the method includes covering a metal sheet on both sides of the processed electromagnetic resistance sheet to prevent the loss of material in physical damage form and loss of signals and battery charge.

According to a third aspect a method for transmission of electrical signals through a electromagnetic resistance sheet is disclosed. According to the third aspect, the method includes receiving an incoming signal from respective towers by a mobile device for grounding and absorption of the electromagnetic frequency generated by the plurality of electric signals.

According to the third aspect, the method includes enabling anti radiation conductive mesh of the electromagnetic resistance sheet to ground friction of electromagnetic waves.

According to the third aspect, the method includes allowing electrical signals to penetrate to the respective mobile device by extracting electromagnetic waves and transmits electric signals.

BRIEF DESCRIPTION OF DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein.

DETAILED DESCRIPTION

Figure 1:
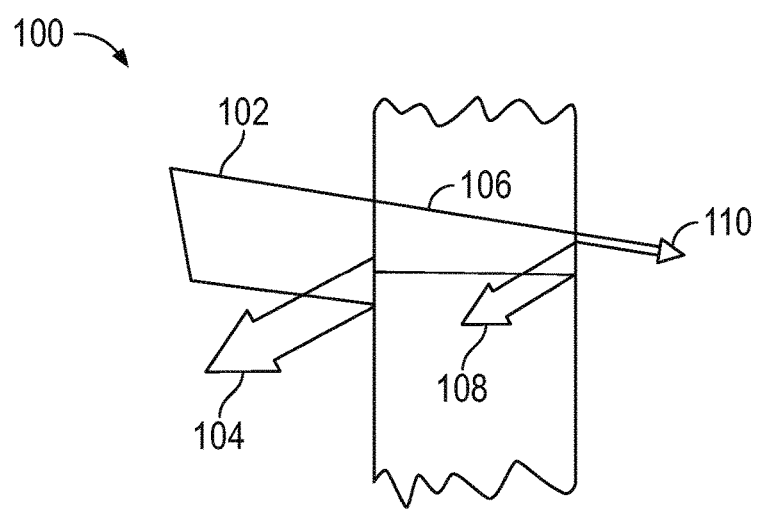
FIG. 1 is a diagram illustrating a electromagnetic resistance sheet used to protect electromagnetic radiations in electronic devices.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

FIG. 1 is a diagram 100 illustrating a electromagnetic resistance sheet used to protect electromagnetic radiations in electronic devices. According to a non limiting exemplary embodiment of the present disclosure, the device used to protect the humans from the exposure of electromagnetic radiations comprising an electromagnetic resistance sheet made with metal based polymer.

As shown in FIG. 1, the metal based polymer sheet 100 receives an electrical signal 102 incorporated with multiple electromagnetic radiations. The metal based polymer sheet 100 consists of three layers, where the first layer coated with chemical element which may include but not limited to nickel or gold is used to block electromagnetic fields, electromagnetic cloud, static cloud generated by electromagnetic waves in process of inducing power by communication system into atmosphere and reflects the static cloud 104 into atmosphere. Also, the metal based polymer sheet 100 includes a second layer made up of polyester fabric which may include but not limited nickel or copper absorbs the signals 106 transmitted from the first layer and decreases the friction of electromagnetic waves by reflecting the electromagnetic radiations 108. The second layer is also enabled as a thermal shield, which observes reduction of heat in communication systems.

Further as shown in FIG. 1, the metal based polymer sheet 100 includes a third layer made of chemical element which may include but not limited to gold or nickel to allow only the required signal by acting as a signal filter and signal repeater. Thus the mechanical sound waves are transferred from the third layer of the metal based polymer sheet 100 by emitting electrical signal or electromagnetic radiations. For convenience, in the present disclosure the first layer and third layer are coated with chemical element gold, which is most electrically conductive of all metals. Since the electricity is essentially the flow of charged particles in a current, metals that are conductive allow this current to flow unimpeded. Thus gold is able to convey even a tiny electrical current in temperature varying from −55 to +220 degrees centigrade. The chemical element gold is also used to ground the high frequency waves emitted by the transmitter. The gold is dense, soft, malleable and ductile metal with an attractive, bright yellow color and luster that is maintained without tarnishing in air or water.

Also further as shown in FIG. 1, for example, the metal based polymer sheet 100 in data communication device which may include but not limited to a mobile phone, tablet and the like. The metal based polymer sheet 100 placed in the data communication device receives an incoming electrical signal transmitted by the user and extracts the electromagnetic waves from the received electrical signals and further transmits only the mechanical sound waves to the respective cell tower of the destination user.

Figure 2:
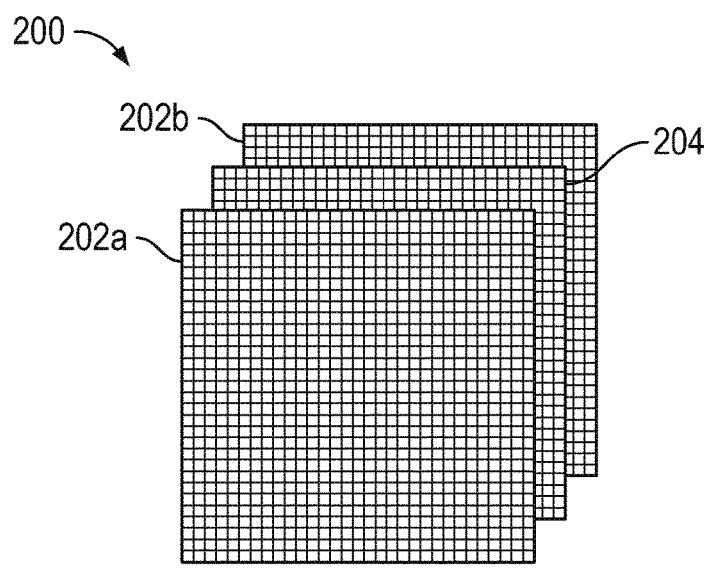
FIG. 2 is a diagram illustrating manufacturing process of conductive mesh of the electromagnetic resistance sheet.

FIG. 2 is a diagram 200 illustrating a formation of conductive mesh of electromagnetic resistance sheet. According to a non limiting exemplary embodiment of the present disclosure, the conductive mesh of the electromagnetic resistance sheet 200 consists of three layers 202a, 202b and 204. As shown in FIG. 2, the first layer 202a and third layer 202b are positioned at the front and rear sides of the electromagnetic resistance sheet. The two first layer 202a and third layer 202b are made up of chemical element gold to convert the received excess radio frequency radiations of electronic signals to electromagnetic field signals and ground the converted electromagnetic field and/or cloud signals for avoiding the transmission of radiations into the human body.

As shown in FIG. 2, the third layer 204 positioned between the first layer 202a and the third layer 202b coated with plurality of metal elements such as nickel and copper to provide anti corrosion of the electromagnetic resistance sheet in the transmission of radiations. The electromagnetic resistance sheet 200 with three layers is referred as a metal based polymer sheet, which is cleansed with chemical element dissoluble in water which may include but not limited to alkaline solution. The cleansed metal based polymer sheet is dipped in a high viscous fluid which may include but not limited to a dilute sulfuric acid in a ratio of 70 parts of water with 30 parts of sulfuric acid comprising a chemical element such as nickel bar of 50 grams. Thus the nickel bar incorporated within the sulfuric acid gets affixed with the dipped metal based polymer sheet to provide a rust proof and anti corrosions.

Also as shown in FIG. 2, a predetermined amount of inorganic compound which may include but not limited to any cyanide such as sodium cyanide, potassium cyanide and the like of 1 liter is mixed in water to form a solution. The predetermined amount of chemical element which may include but not limited to gold of 2.5 grams is attached to the cathode and anode is hanged free in the mixed sodium cyanide solution and boiled to a high temperature of 375 degrees to dissolve the gold attached at the cathode in the solution and forms a light yellow solution. Further the metal based polymer sheet with anode of one meter is dipped in the still hot 110 degrees centigrade solution to transmit the power to the sheet. Along with the transmission of the power the gold incorporated in the solution is transmitted to the metal based polymer sheet treated with nickel and leaves the color less water. Thus the first layer 202a and third layer 202b are formed with gold coating and second or middle layer 204 is remained with the nickel coating.

Further, the goal coated metal based polymer sheet is perfectly cleansed to remove the sodium cyanide present on the sheet, which is highly toxic to biological health and also leads to the death of humans. Also further the metallic polymer sheet is covered with a metal sheet which may include but not limited to a aluminum, lead, tin, uranium and the like on both sides to make sure that the sheet is working properly without disrupting signals and also prevent the loss of material in physical damage, loss of signal and battery charge. Thus the processed electromagnetic resistance sheet absorbs electromagnetic waves and transmits electric signals without any loss of quality through point of origin and point of destination and acts as a signal booster and electromagnetic field grounding substance. Further the first layer 202a and third layer 202b used to multiply signals and second layer 204 is used to ground and absorb electromagnetic field generated at point of origin and point of destination. Also further the processed electromagnetic resistance sheet acts as mesh antenna to receive the electromagnetic waves for filtering and transmitting the electrical signals to the receiver.

Figure 3:
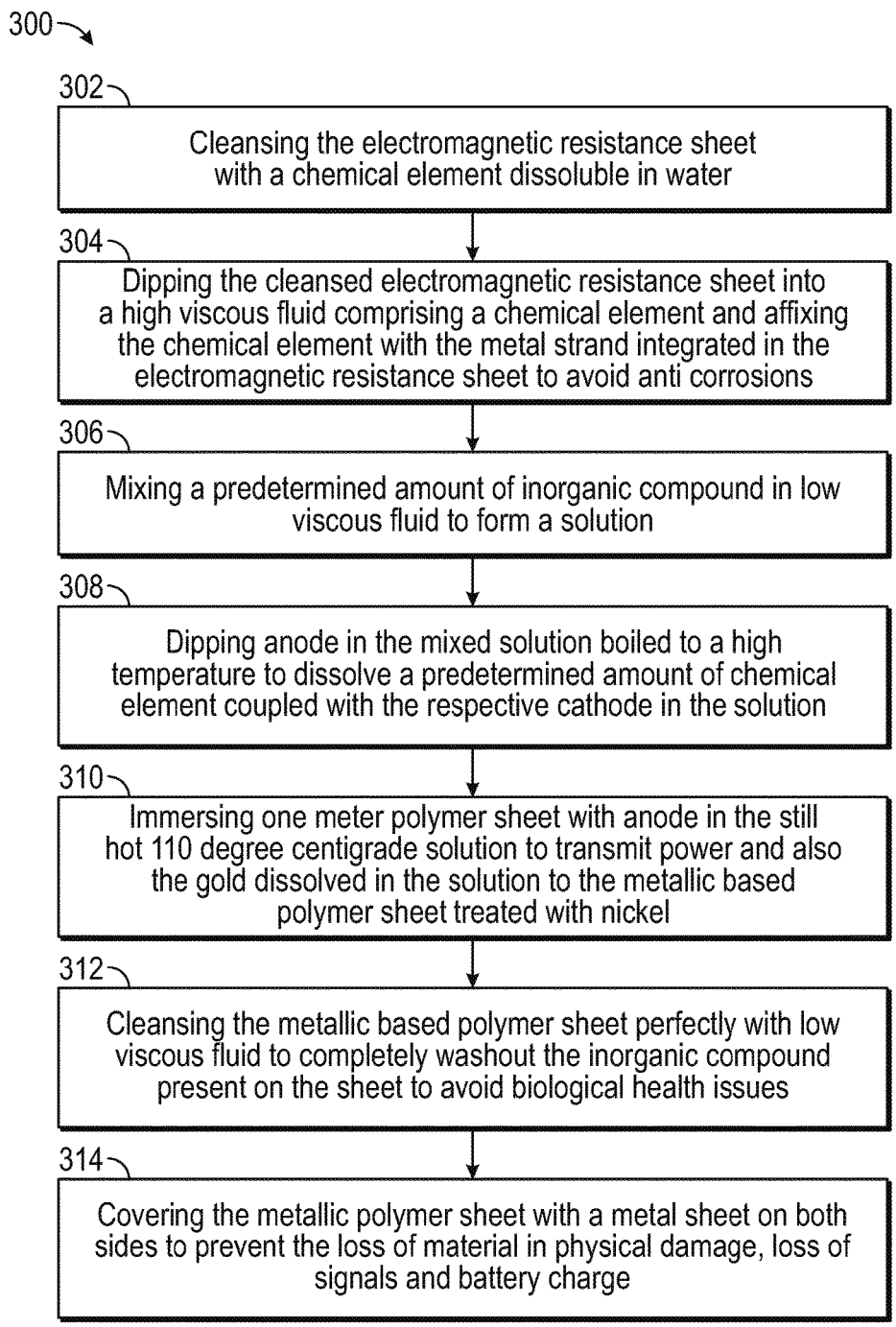
FIG. 3 is a flow diagram illustrating a method of manufacturing a electromagnetic resistance sheet to avoid the transmission of electromagnetic waves.

FIG. 3 is a flow diagram 300 illustrating a method of manufacturing an electromagnetic resistance sheet to avoid the transmission of electromagnetic waves. According to a non limiting exemplary embodiment of the present disclosure, the method of manufacturing electromagnetic resistance sheet starts at step 302 by cleansing the electromagnetic resistance sheet with a chemical element dissoluble in water. Next at step 304, the cleansed electromagnetic resistance sheet is dipped into a high viscous fluid which may include but not limited to a dilute sulfuric acid comprising a chemical element such as nickel bar and affix the nickel bar with the metal strand integrated in the electromagnetic resistance sheet to avoid anti corrosions.

As shown in FIG. 3, at step 306 a predetermined amount of inorganic compound such as sodium cyanide of 1 liter is mixed in low viscous fluid such as water to form a solution. Next at 308 a predetermined amount of chemical element gold is coupled with cathode and the respective anode is dipped in the mixed solution boiled to a high temperature of 375 degrees centigrade to dissolve the chemical element gold in the solution and forms a light yellow color solution. Further at step 310, the one meter polymer sheet with anode is dipped in the still hot 110 degree centigrade solution to transmit power to the sheet. Along with the power, gold dissolved in the solution is also deposited over the metallic based polymer sheet treated with nickel and leaves the color less solution. Also further at step 312, the metallic based polymer sheet is cleansed perfectly with low viscous fluid such as water to completely washout the inorganic compound present on the sheet deposited along with the gold to avoid biological health issues which especially may also lead to the death of the human. Moreover at step 314, the metallic polymer sheet is covered with a metal sheet which may include but not limited to aluminum, lead, tin and the like on both sides of the processed electromagnetic resistance sheet to prevent the loss of material in physical damage, loss of signals and battery charge.

Figure 4:
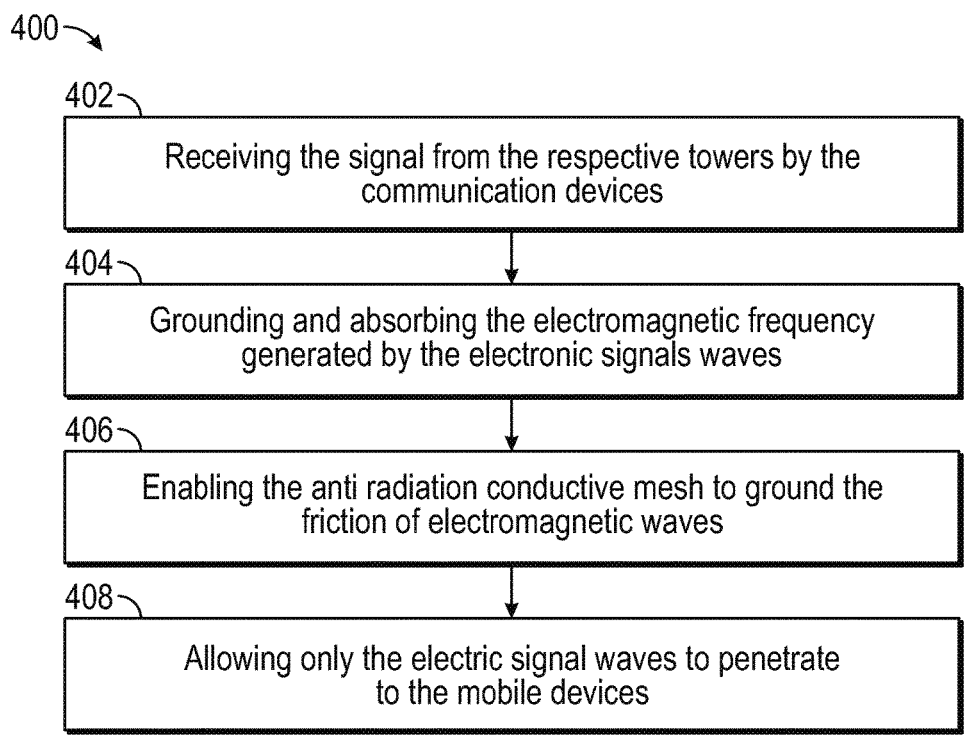
FIG. 4 is a flow diagram illustrating a method of transmission of electrical signals through a electromagnetic resistance sheet.

FIG. 4 is a flow diagram 400 illustrating a method of transmission of electrical signals through a electromagnetic resistance sheet. According to a non limiting exemplary embodiment of the present disclosure, the method starts at step 402 by receiving a signal from the respective towers by the communication device and grounds and absorbs the electromagnetic frequency generated by the electronic signal at step 404. Further at step 406, the anti radiation conductive mesh is enabled to ground the friction of electrical signals and allow the electrical signals to penetrate to the mobile devices at step 408.

While specific embodiments of the disclosure have been shown and described in detail to illustrate the inventive principles, it will be understood that the disclosure may be embodied otherwise without departing from such principles.

What is claimed is:

1. A device used to reduce electromagnetic radiations, comprising:
   an electromagnetic resistance sheet comprising:
      a first layer; and a third layer positioned at front and rear portions of the electromagnetic resistance sheet configured to convert received excess radio frequency radiations of electronic signals to the electromagnetic field signals; and ground the converted electromagnetic field; and cloud signals for avoiding the transmission of radiations into the human body, wherein the first layer; and the third layer coated with plurality of chemical elements; and
      a second layer positioned between the first layer; and the third layer coated with plurality of metal elements to provide anti corrosion of the electromagnetic resistance sheet in the transmission of radiations.

2. The device of claim 1, wherein the electromagnetic resistance sheet forms a conductive mesh made with metal strands woven into the construction of the mesh with chemical elements.

3. The device of claim 2, wherein the metal strands comprising a copper; and nickel used to form conductive mesh.

4. The device of claim 2, wherein the metallic elements comprising a silver; and gold.

5. The device of claim 2, wherein the conductive mesh affixed to electronic equipments to avoid the transmission of electromagnetic radiations into the human body.

6. The device of claim 1, wherein absorbs electromagnetic waves and transmits electric signals without any loss of quality through point of origin; and point of destination; and represented signal booster.

7. The device of claim 1, wherein including a first layer; and third layer configured to multiply signals; and second layer capable of grounding; and absorption of electromagnetic field generated at point of origin; and point of destination.

8. The device of claim 1, wherein a processed electromagnetic resistance sheet represents a mesh antenna to receive electromagnetic waves for filtering and transmitting the required electric signals to receivers.

9. A method to reduce electromagnetic radiations, comprising:
   cleansing a electromagnetic resistance sheet with a chemical element dissoluble in water; and dipped into a high viscous fluid comprising a chemical element, wherein a metal strand integrated in the electromagnetic resistance sheet affixed with the chemical element of the high viscous liquid to avoid anti corrosions;
   mixing a predetermined amount of inorganic compound in low viscous liquid to form a solution, wherein a predetermined amount of chemical element coupled with cathode; and anode dipped into the mixed solution to dissolve the chemical element in the viscous liquid and forms a light yellow solution;
   inserting a predetermined length of the electromagnetic resistance sheet coupled with anode into the boiled solution, wherein the electromagnetic resistance sheet receives power from the boiled solution along with the chemical element dissolved in the solution and leaves the color less solution;

cleansing the electromagnetic resistance metallic sheet with low viscous liquid to completely cleanse out the inorganic compound on the electromagnetic resistance sheet received from the chemical element dissolved in the solution for protecting the biological health of the human; and environment; and covering a metal sheet on both sides of the processed electromagnetic resistance sheet to prevent the loss of material in physical damage; loss of signals; and battery charge.

10. A method for transmission of electrical signals through a laminated sheet, comprising: receiving an incoming signal from respective towers by a communication device for grounding; and absorption of the electromagnetic frequency generated by the plurality of electric signals; enabling anti radiation conductive mesh of the electromagnetic resistance sheet to ground friction of electromagnetic waves; and allowing electrical signals to penetrate to the respective mobile device by blocking electromagnetic waves and transmitting electric signals.

* * * * *